United States Patent [19]

Beck

[11] Patent Number: 5,309,904
[45] Date of Patent: May 10, 1994

[54] INSUFFLATING/SUCTIONING VALVE

[76] Inventor: Blaine E. Beck, 1895 Ledieu Rd., Roswell, Ga. 30075

[21] Appl. No.: 22,179

[22] Filed: Feb. 25, 1993

Related U.S. Application Data

[63] Continuation of Ser. No. 646,581, Jan. 28, 1991, Pat. No. 5,191,881.

[51] Int. Cl.$^5$ .............................................. A62B 9/02
[52] U.S. Cl. .......................... 128/205.24; 128/207.16
[58] Field of Search ...................... 128/204.18, 205.24, 128/207.16; 251/9; 137/596, 596.2

[56] References Cited

U.S. PATENT DOCUMENTS 3,918,490  11/1975  Goda ......................................... 251/9
4,193,406   3/1980  Jinotti ................................ 128/204.18

Primary Examiner—Edgar S. Burr
Assistant Examiner—Aaron J. Lewis
Attorney, Agent, or Firm—Schweitzer Cornman & Gross

[57] ABSTRACT

An insufflating/suctioning valve having a valve body containing fluid flow controlling members which are two resilient plastic tubes, a spring-biased actuating mechanism having three positions to control flow or to shut off flow in each tube, or to shut off flow simultaneously in both tubes.

7 Claims, 3 Drawing Sheets

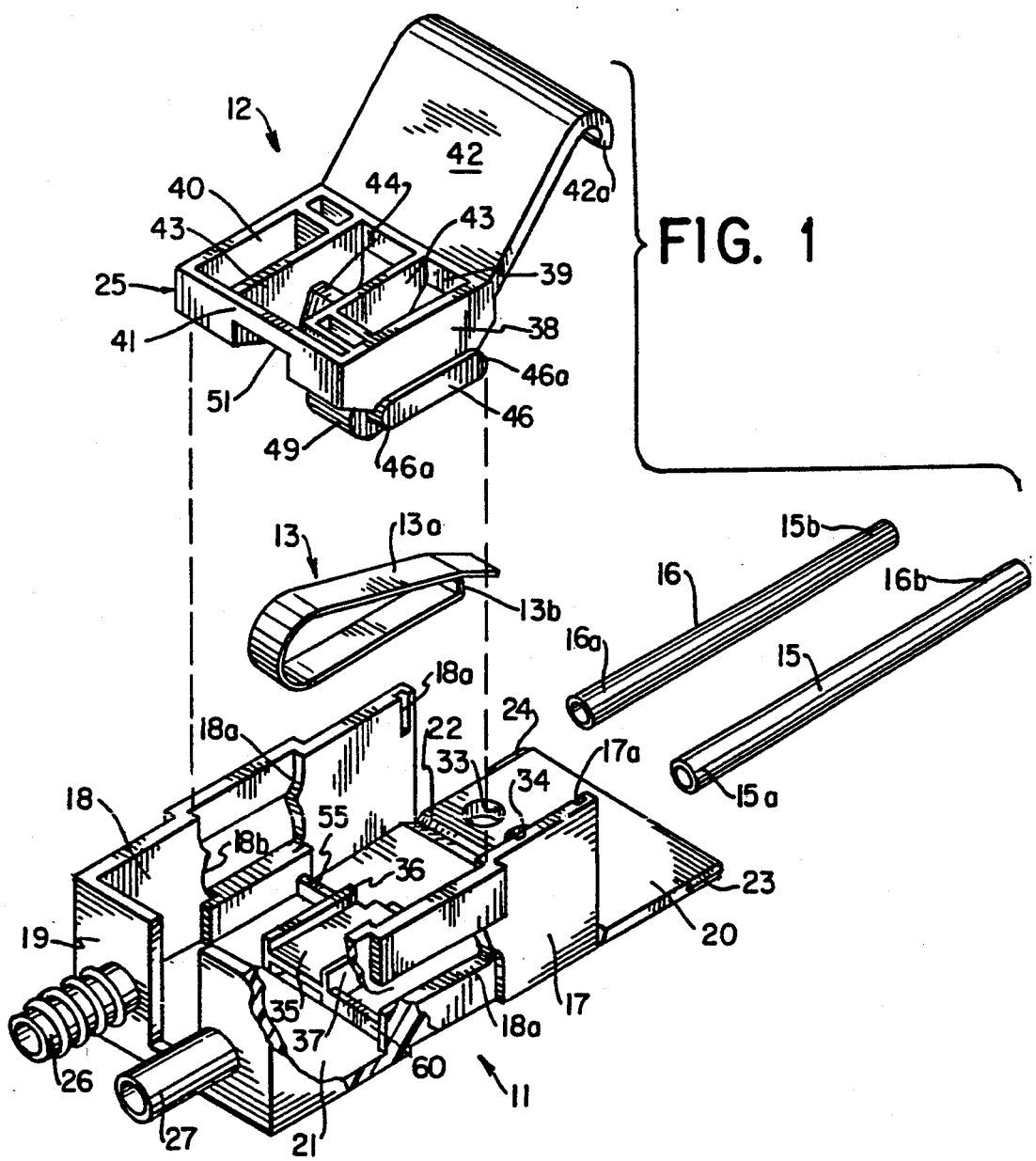

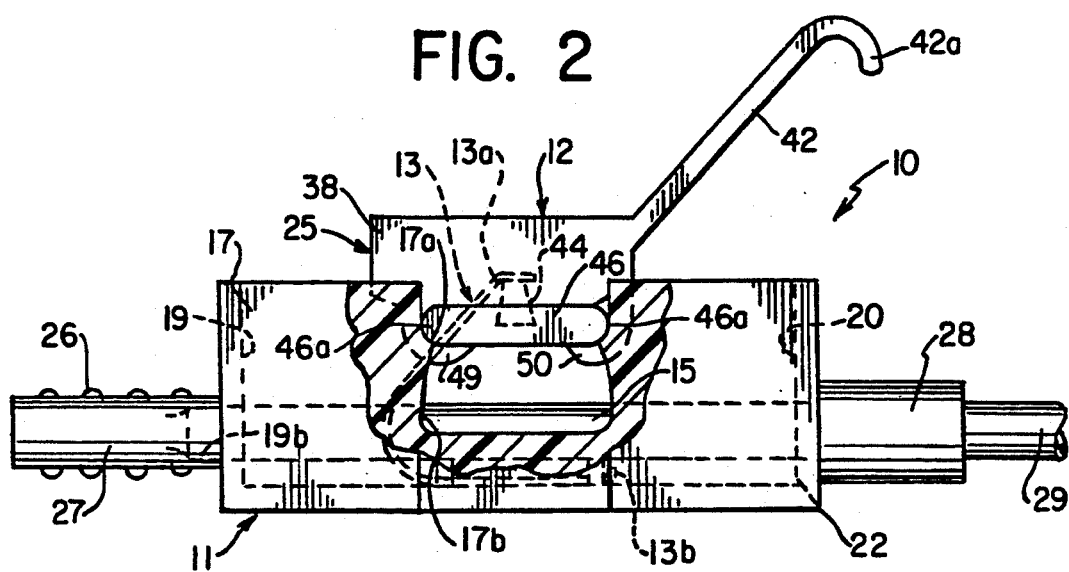
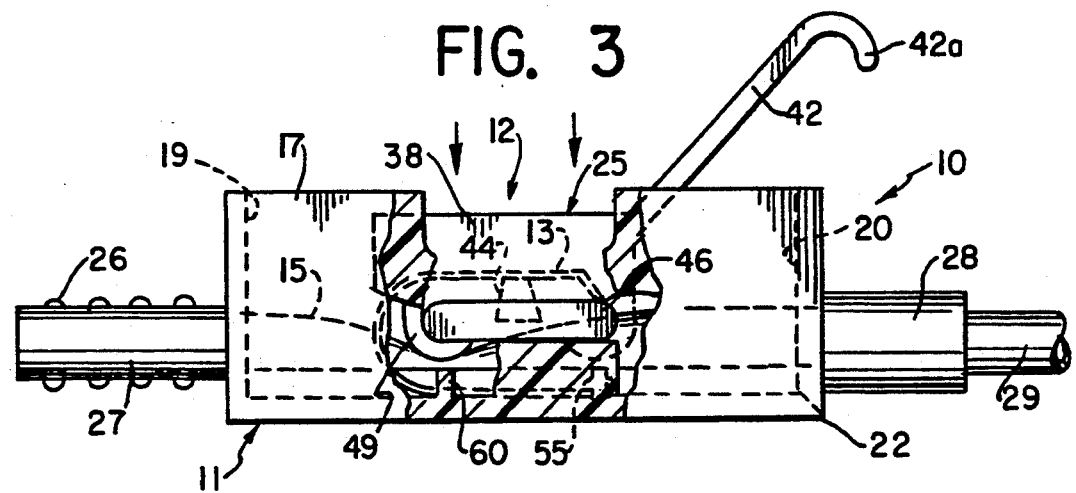
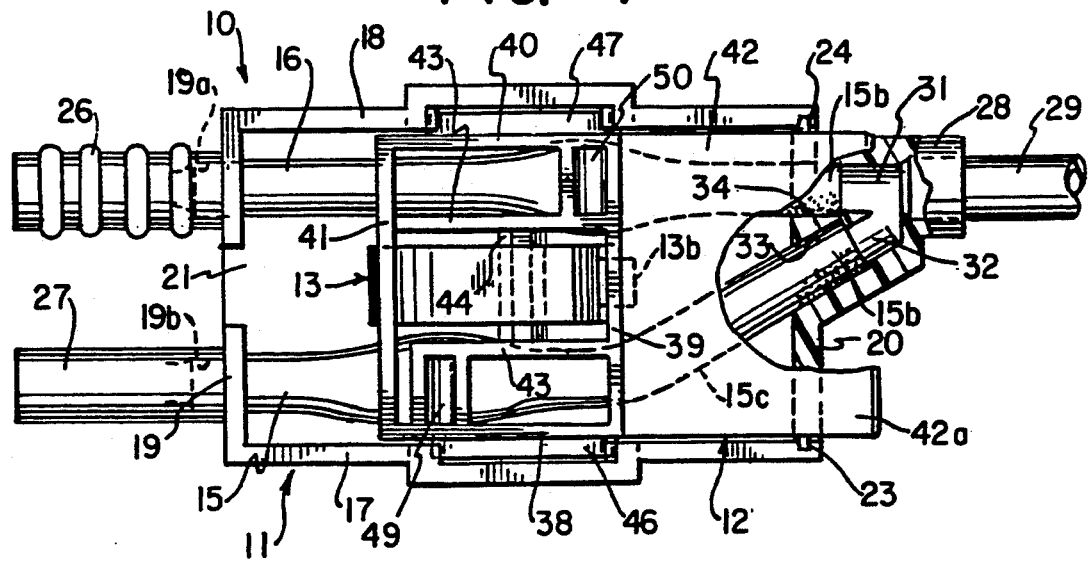

INSUFFLATING/SUCTIONING VALVE

RELATED APPLICATION

This application is a continuation of Ser. No. 07/646,581, filed Jan. 28, 1991, now U.S. Pat. No. 5,191,881.

BACKGROUND OF THE INVENTION

The present invention finds application in carrying out those medical procedures where it has become necessary to remove fluid from the tracheal regions of persons who otherwise would be placed in a life threatening situation. Suctioning catheters have for many years been used for this purpose but are beginning to be superseded by insufflating/suctioning valves, that is, valves which alternatively provide fluid suctioning and oxygenation (insufflation) of the tracheal region.

Examples of various known insufflation and suctioning valves may be seen in U.S. Pat. Nos. 4,705,073, 4,193,406, 4,595,005 and 4,300,550. The advantage which valves of this type have in comparison with suctioning catheters is enormous, since both oxygen to replace that removed during suctioning and fluid removal by suction are supplied by the same device; whereas the use of suctioning catheters requires a separate, less controlled and therefore hazardous administration of oxygen to the patient. The principal advantage which may be attributed to the use of suctioning catheters is their cost, which is a fraction of that of insufflation valves currently being marketed.

SUMMARY OF THE INVENTION

The present invention comprises a valve of extremely simple and fool-proof design, having a cost which can compete with suctioning catheters, while including improved features not found in state-of-the-art insufflation suctioning valves in use today. The valve of the invention comprises only four essential parts, three of which are stationary: the valve body, two pieces of plastic tubing and a spring. The only moving part is the valve actuating mechanism which is molded of a single piece of plastic as is the valve body. Consequently the cost of manufacture and assembly is extremely low.

Operational improvements which may be attributable to the valve of the present invention in contrast to those heretofore known are the following: a) valve action i.e. alternatively applying suction to a single catheter connecting the valve to the tracheal region of a patient, or oxygenation of such regions is completely and efficiently achieved by a valve actuating mechanism which alternatively crimps closed each of two resilient tubes which connect respectively with a source of suction and a source of oxygen; b) fully shut off position of tubes intermediate switching from one tube operative position to another; c) complete sealing of interior of valve from contamination of suctioned fluid; and minimal cost of manufacture competitive with suctioning catheters.

BRIEF DESCRIPTION OF THE DRAWING

FIG. 1 is an exploded perspective view of the valve which embodies the invention as described herein;

FIG. 2 is a side view, partially broken away, of the valve shown in FIG. 1, with the valve actuating mechanism and other components thereof in position for shipping;

FIG. 3 is a side view of the valve of the invention with the valve actuator mechanism in the fully shut off position;

FIG. 4 is a top view of the valve of the invention (partially broken away) in the position shown in FIG. 3;

DESCRIPTION OF THE DISCLOSED EMBODIMENT

Figure 5:
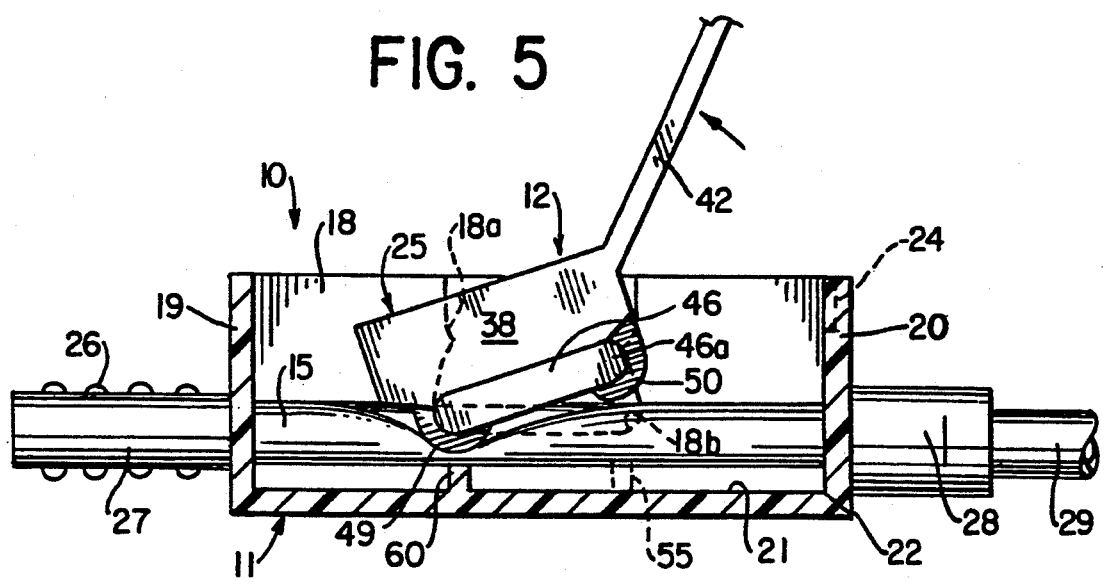
FIG. 5 is a side view of the valve of FIG. 1 showing the interior thereof with the valve actuator mechanism in position to crimp shut one of the fluid tubes therein while the other of the tubes remains open to flow.

Referring now to the drawing and initially to FIG. 1, thereof, an insufflating valve 10 incorporating the present invention has been illustrated in exploded form. Included in the valve 10 is a valve body 11 and valve actuating mechanism 12, each of which has been molded of suitable plastic material. The valve 10 further includes a metal spring 13 and incorporates within the valve body 11 plastic tubing 15 and 16.

The valve body 11 is essentially a rectangular box having side panels 17, and 18, end panels 19, 20 and a base 21, the interior of the body having been molded to receive and cooperate with the valve actuating mechanism 12, spring 13 and tubes 15 and 16. Tubes 15 and 16 are preferably composed of polyvinyl chloride having a wall thickness of 0.010"–0.015" (ten-15 thousandths) of an inch. This dimensional thickness permits tubes 15 and 16 to be temporarily sealed shut (with respect to fluid flow therein) by being crimped while retaining requisite resilience to return to a tubular fluid flow position. End panel 20 of the valve body 11 is connected to the base 21 by a thin resilient integrally connecting strip of plastic which serves as a "living" hinge 22 to permit the alternate upright positioning of end panel 20 as shown in FIG. 2 and in the remaining figures. Each of the base 21 and end panel 20 are mitered adjacent to hinge 22 to achieve a close fit when end panel 20 is in its upright position. End panel 20 may be swung into the upright position against and within side panels 17 and 18 which together with the side panels and base 21 will comprise a rectangular box like structure. End panel 20 and side panels 17 and 18 have been provided with mating locking means 23, 24 (protruding from the edge of end panel 20) and grooves 17a, 18a (in side panels 17 and 18) to secure end panel 20 in the upright position.

Permitting end panel 20 to extend adjacent to base 21 as shown in FIG. 1, provides access to the interior of valve body 11 for assembly therein of tubes 15 and 16. End panel 19 has been provided with tubular fluid connectors 26, 27 which may be connected individually to a source of oxygen and to a suction source. For purposes of illustration, connector 26 shall be described herein as being adapted to be connected to an oxygen source and connector 27 to a source of suction. It will be understood that this is arbitrary and for purposes of this description, as is the design of connectors 26 and 27 as illustrated.

Referring to FIG. 4 it will be seen that the outwardly facing side of end panel 20 has been molded as a connector 28 which is adapted to receive therein catheter 29 in fluid tight relationship. Connector 28 has internally formed cylindrical passages 31, 32 which respectively connect with inwardly facing openings 33, 34 in end panel 20.

Figure 7:
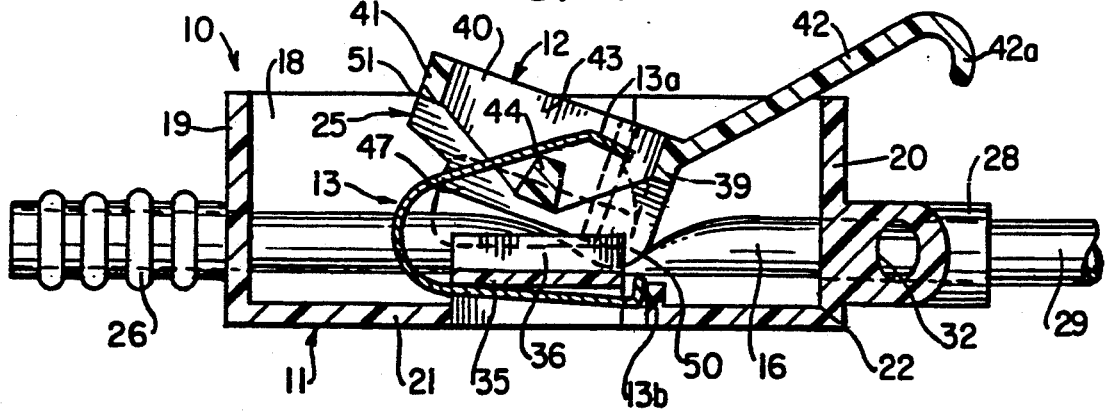
FIG. 7 is a view which illustrates the spring action of the valve actuator mechanism during the crimping action of FIG. 6.

Tubes 15 and 16 are located and assembled within the valve body 11 as follows: While end panel 20 is in the position shown in FIG. 1, the ends 15a and 16a of tubes 15 and 16 are first connected to end panel 19 by being received into cylindrical recesses 19a and 19b (see FIG. 4). Such connection will normally be secured by adhesive and thus tubes 15 and 16 shall be connected in fluid tight relation with external connectors 26 and 27. Next, the opposite ends 15b and 16b of tubes 15, 16 are received respectively in openings 33, 34 (see FIG. 4) in the internally facing side of end panel 20 which is swung upwardly toward tube ends 15b and 16b to permit such contact. Tube ends 15b, 16b shall be adhesively joined to the adjacent structure of the connector 28 which defines passages 31, 32. A straight-through connection of tube 16 within valve body 11 is thus achieved between connectors 26 and 28. It will be seen that tube 15 must bend somewhat at 15c in order to have end 15b thereof proceed through opening 33 and into passage 32. As best seen in FIG. 1, valve body 11 has been provided with vertical ribs 36 and 37 which are joined by a transverse horizontal joining section 35 (FIGS. 1 and 7). Tubes 15 and 16 are positioned along opposite sides of sections 36 and 37 immediately above short vertical abutments 55 and 60. When tubes 15 and 16 are assembled therein as described, rib 37 directs and maintains the direction of tube 15 as it is bent forward and into passages 33 and 32.

Referring now to the valve actuating mechanism 12, such mechanism comprises a main generally oblong shaped section 25 defined by sides 38, 39, 40, and 41. Integrally formed along the upper edge of side 39 is an actuating arm 42, having a curved end 42a. Section 25 is stiffened and reinforced internally by lateral walls collectively denominated by reference numeral 43 while a truncated pyramidally shaped member 44 extends generally perpendicularly from the lateral stiffeners 43 of the main section 25 whose function is to interrelate with spring 13 as shall be described.

Sides 38 and 40 each are integrally connected to laterally projecting elongated bosses 46, 47 having rounded ends 46a, 47a which in the assembled positions shown in FIGS. 2-7 are alternatively received within correspondingly shaped recesses 17a, 17b and 18a, 18b in sides 17 and 18. Projecting downward from the base 25 of actuating mechanism 12 are two curved sections 49 and 50 each of which projects from the base 25 adjacent to diametrically opposite corners of sides 38 and 40. A generally rectangular channel 51 is formed in base 25 which straddles sections 36 and 37 in the valve body when the parts are in their fully operative position.

FIG. 2 illustrates the shipping position of the valve 10. In this position bosses 46 and 47 are retained within recesses 17a and 18a of sides 17 and 18 of the valve body 11. As shown in FIG. 7, the flat section 13a of spring 13 engages and presses upon the top of member 44 in the actuating mechanism 12 while the curved lower end of spring extends beneath horizontal section 35 and tang 13b of spring 13 extends upwardly outside of section 35 to lock the spring in place.

To place the actuating mechanism 12 in its operative position, the mechanism arm 42 is pushed upwardly to rotate bosses 46 and 47 in upper recesses 17a and 18a until the rounded ends 46a, 47a clear these recesses, which allows bosses 46, 47 to snap into lower recesses 17b, 18b under pressure of spring 13. If arm 42 is then released, the position of the valve actuating mechanism 12 shall automatically be that shown in FIG. 3. When the actuating mechanism 12 is in this position, sections 49 and 50 will crimp both tubes 15 and 16 against abutments 60 and 55, such crimping action being sufficient to totally shut off the possibility of fluid flow through tubes 15 and 16.

FIG. 5 illustrates the effect of rotating the actuating arm 42 of actuating mechanism 12 in a counterclockwise direction from the position shown in FIG. 3 In the position of FIG. 5, pressure from section 50 against abutment 55 has been relieved to permit flow through tube 16 while tube 15 is crimped shut by pressure from section 49 against abutment 60.

It is an important safety feature of the present invention that when pressure is released from arm 42 when in the position shown in FIG. 5, the valve actuating mechanism 12 will automatically be caused by action of spring 13 to return to the full shut-off position of FIG. 3.

Figure 6:
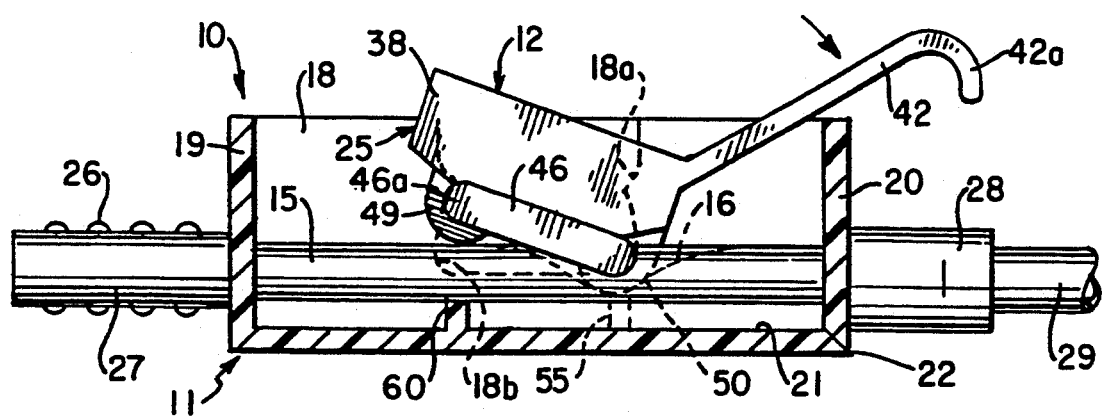
FIG. 6 is a view similar to FIG. 5 in which the valve actuator mechanism has crimped shut the other of the tubes shown in FIG. 5 while permitting the crimped tube of FIG. 5 to be open.

In the position of FIG. 6 arm 42 has been rotated clockwise so that tube 15 is open to flow while tube 16 is crimped shut. Thus, by a simple rocking motion of actuating arm 42 either of tubes 15, 16 may be crimped shut to flow while the other of such pair may be open to flow. It should be noted that it is an additional safety feature of the present invention that in order to proceed from suctioning to insufflating (oxygenation) suctioning is shut off entirely before insufflation can begin. For example, after suctioning fluid from the tracheal regions of a patient by the use of suction through tube 15 and catheter 29, should the therapist or physician wish to insufflate oxygen through catheter 29 into such tracheal region, arm 42 must first be moved through the intermediate position of FIG. 3 which makes flow impossible through either tube 15 or 16. This means that the therapist cannot position flow of the valve directly from suctioning to insufflation inadvertently or otherwise. During the suctioning mode, fluids from the tracheal region pass from the catheter 29 through the valve 10, through a source of suction (not shown) and are collected for disposal. Some fluid invariably remains in the catheter 29 and therefore, according to current procedures, the catheter is gradually withdrawn from the tracheal region for 10–15 seconds to allow most of the fluid to be collected as just described. Prior to inserting the catheter into the tracheal region again, the therapist or physician will place the distal end of the catheter into a receptacle and slowly allow oxygen to flow through the catheter to drive any remaining fluid therefrom without sudden discharge or spitting which can be hazardous to attending personnel. The present valve construction insures the degree of control necessary for this operation. Also, it will be noted that the use of tubing to control fluid flow through valve 10 prevents internal leakage and contamination within the valve body between sections devoted to suctioning and oxygenating. Positive pressure is maintained at all times in oxygen tube 16 upstream of the shut-off (crimp) point. Consequently, only a short section of tube 16 is exposed to fluid suctioned into tube 15 and such fluid is ejected during the catheter clearing procedure described. No suctioned fluid may leak into the interior of valve 10 so long as adhesive bonding of tubes 15, 16 is done properly. In other conventionally designed valves employing O-rings and the like, some leakage and therefore contamination is inevitable.

The various features and advantages of the present invention as described herein include: a) positive control at all times of the operative suctioning and oxygenation positions of the valve; b) release of the actuating mechanism by the operator causing automatic shut off of all flow function; c) proceeding from the oxygenation mode to suctioning mode must include intermediate shut off of all valve flow function; d) shipping position of valve components protects tubing from being compressed until the valve is rendered operational; e) no moving sealing parts other than flexed tubing to effect flow of oxygen and suction;—therefore there is no leakage across internal valve seals; f) other potential internal leakage within valve body is prevented by fixed adhesive sealing of tubes to valve body passage walls; g) valve consists of five parts: two tubes, a valve body, a valve actuator and a spring; and the only moving parts are the valve actuator and flexing movement of the tubing and spring and h) all parts are easily and inexpensively manufactured and assembled to produce a valve which is competitive in price with suctioning catheters.

It will be understood that the foregoing description has been of a particular embodiment of the invention and is representative thereof. In order fully to appreciate the scope of the invention, reference should be made to the appended claims.

What is claimed and desired to be secured by U.S. Letters Patent is:

1. An insufflating valve comprising:
   a) a valve body;
   b) two fluid connectors attached externally to said valve body and a catheter connector extending externally from said body;
   c) two hollow resilient plastic tubes extending through the interior of said body and interconnecting in fluid tight relationship each of said fluid connectors to said catheter connector;
   d) valve actuating means for selectively shutting off fluid flow by crimping each of said tubes and for permitting flow therethrough by discontinuing said crimping;
   e) abutment means transversely of and in contact with each of said plastic tubes;
   f) said valve actuating mechanism including two tube contact means each being adapted to be in contact with one of said tubes and such that said tubes are between said abutment means and said tube contact means and an actuating arm connected to said tube contact means, said arm extending from said valve body;
   g) movement of said actuating arm into a first position effecting movement of one of said tube contact means toward one of said abutment means to cause crimping of one of said tubes to prohibit fluid flow therethrough; said movement of said actuating arm also effecting movement of the other of said tube contact means away from the other of said abutment means;
   h) movement of said actuating arm into a second position effecting movement of the other of said tube contact means into contact with the other of said abutment means to cause crimping of the other of said tubes and the release of the first of said tube contacting means from crimping contact with the first of said abutment means;
   i) movement of said actuating arm into a third position effecting crimping movement of both tube contacting means against both abutment means to prevent fluid flow through both of said tubes;
   j) said third position of said actuating arm being intermediate said first and second positions; and
   k) said valve actuating mechanism is spring-biased toward said third position such that said actuating arm will automatically seek said third position upon release of said actuating arm.

2. The valve of claim 1 wherein said valve actuating mechanism defines two elongated bosses having rounded ends projecting in opposite directions therefrom, said valve body defining mating recess means to receive said bosses, rotating movement of said actuating arm causing corresponding rotating movement of said actuating mechanism, sid tube contacting means being located on said actuating mechanism to cause alternate tube crimping contact and release of said tube crimping contact in each of two operative positions of said actuating arm.

3. The valve according to claim 2 wherein movement of said actuating arm between individual tube crimping contact positions places said arm in an intermediate position in which both tubes are crimped closed to fluid flow at the same time.

4. The valve according to claim 3 in which said valve body and valve actuating mechanisms are molded entirely of plastic.

5. The valve according to claim 4 wherein said valve body defines first and second recess means, said first recess means being adapted to cooperate with said bosses to permit crimping of said tubes, said second recess means being disposed further from said tubes than said first recess means a distance sufficient to maintain said contacting means out of contact with said tubes, said first and second recess means being formed to connect with each other to permit said elongated bosses of said actuating mechanism to move between said second and first recess means.

6. The valve according to claim 5 wherein said valve actuating mechanism nests within said valve body and is secured therein entirely by contact of said bosses within said recess means, and a spring intermediate said valve body and said actuating mechanism to apply resilient force therebetween to maintain said contact, said bosses and recess means being shaped as interrelated cam surfaces to cause said actuating mechanism to be returned automatically to said intermediate position when said actuating arm is released.

7. The valve according to claim 6 wherein said valve body and valve actuating mechanism are each respectively of one piece, molded plastic construction and said valve entirely consists of said valve body, said actuating mechanism, two plastic tubes and a spring.

* * * * *